United States Patent [19]

Campbell et al.

[11] 4,406,392

[45] Sep. 27, 1983

[54] SURGICAL STAPLING INSTRUMENT

[75] Inventors: Jay E. Campbell, Upper Black Eddy; Richard H. Reichmann, Churchville, both of Pa.; Lehmann K. Li, Fairfield, Conn.

[73] Assignee: American Cyanamid Company, Stamford, Conn.

[21] Appl. No.: 191,654

[22] Filed: Sep. 26, 1980

Related U.S. Application Data

[63] Continuation-in-part of Ser. No. 153,228, May 27, 1980, abandoned.

[51] Int. Cl.³ .............................................. A61B 17/04
[52] U.S. Cl. ........................................ 227/19; 227/83;
227/156; 227/DIG. 1
[58] Field of Search .................... 72/410; 128/334 R;
227/19, 83, 107, 114, 115, 116, 119, 120, 121,
139, 149, 156, DIG. 1

[56] References Cited

U.S. PATENT DOCUMENTS

| 2,707,783 | 5/1955 | Sullivan | 227/DIG. 1 |
|---|---|---|---|
| 3,873,016 | 3/1975 | Fishbein | 227/DIG. 1 |
| 3,905,535 | 9/1975 | Novak et al. | 227/120 |
| 4,043,504 | 8/1977 | Hueil et al. | 227/116 |
| 4,109,844 | 8/1978 | Becht | 227/120 |
| 4,179,057 | 12/1979 | Becht et al. | 227/19 |
| 4,196,836 | 4/1980 | Becht | 227/110 |
| 4,202,480 | 5/1980 | Annett | 227/8 |

Primary Examiner—Paul A. Bell
Attorney, Agent, or Firm—Charles F. Costello, Jr.

[57] ABSTRACT

A surgical stapling instrument comprising a handle and a trigger pivotally attached and on compression internal to the handle has been invented. The forward portion of the handle contains: a track; a plurality of staples loaded and staple advancing means carried on the track; a track cover mounted onto the track; and an anvil surface mounted and a first bias means movably mounted on the cover. The anvil surface terminates in a perpendicular flange. The forwardmost staple is adjacent the anvil surface. A retainer spring supports the staple and separates it from the perpendicular flange. The staple is formed on the flange.

The forward portion of the handle also contains a guide block which is mounted on the track cover adjacent the anvil surface. A forming blade and a second bias means are movably mounted on the guide block. The forming blade and the trigger have coordinating surfaces.

On compressing the trigger into the handle, the forming blade pushes the staple downward, the staple displaces the retainer spring and the staple forms on the flange. The retainer spring moves back to its initial position. On releasing the trigger and advancing the instrument the formed staple is separated from the flange. The second bias means returns the trigger and the forming blade to their initial positions.

4 Claims, 29 Drawing Figures

SURGICAL STAPLING INSTRUMENT

CROSS REFERENCE TO RELATED APPLICATION

This is a continuation-in-part application of U.S. application Ser. No. 153,228, filed May 27, 1980, now abandoned.

BACKGROUND OF THE INVENTION

This invention relates to a surgical skin/fascia stapling instrument which contains a plurality of staples and which allows a single staple to be formed and removed from the instrument.

To develop the background of the invention and to establish the state of the art, the following references are cited: U.S. Pat. Nos. 4,179,057; 4,109,844; and 3,873,016, which are incorporated by reference. These references disclose stapling instruments which contain a plurality of staples and from which a single staple can be formed and removed.

The stapling instrument of this invention has advantages over these prior art references. One advantage is the relative size of the instrument which is maintained while the number of mechanical parts is decreased. Therefore, as a general statement, the ease of operation and the reliability of the instrument is improved. The operation and reliability of an instrument can be critical in the surgical operating area where even seconds may determine if a surgical operation or procedure is a success. Another advantage is the orientation of the flange on the anvil surface. The flange orientation is opposite to the direction of stapling. For most surgeons, the natural direction of stapling is always away from their body. The orientation of the flange allows the surgeon to advance the instrument and remove the formed staple in a direction away from the body. This has still another advantage in that while stapling the surgeon cannot accidentally brush against the open wound site.

Still another advantage of this instrument is the stapling indicator which is on top of the handle. The instrument thus does not have to be turned over to determine the number of staples remaining in the instrument. Still further, another advantage is the location of the trigger means which are internal to the handle. This seems to provide a more sterile environment and to prevent or decrease the liklihood of pinching a finger or fingers during use. Yet another advantage is the configuration of the instrument. In many surgical procedures, the instrument configuration may give a better field of vision of the wound site to the surgeon.

The surgical stapling control means also has advantages over the prior art references. The control means prevents the trigger from returning to its initial position if the compression is interrupted. Thus has the advantage of preventing a second staple from being formed on the anvil flange before a first staple is separated from the instrument. Another advantage of the control means is interrupted stapling. The surgeon can now stop the compression of the trigger into the handle to realign the instrument over the wound site. Thus the possibility of a perfect stapling procedure is greatly enhanced.

SUMMARY OF THE INVENTION

A surgical stapling instrument comprising a handle and a trigger pivotally attached and on compression internal to the handle has now been invented. The forward portion of the handle contains a track; a plurality of staples loaded and staple advancing means carried on the track; a track cover mounted on the track; an anvil surface mounted and a first bias means movably mounted on the cover, the anvil surface terminating in a perpendicular flange; a staple adjacent the anvil surface; and a retainer spring mounted on the anvil surface and separating the staple from the flange.

The forward portion of the handle also contains a guide block which is mounted on the track cover adjacent the anvil surface.

A forming blade and a second bias means are movably mounted on the guide block, the forming blade and the trigger having coordinating surfaces.

On compressing the trigger into the handle, the forming blade pushes the staple downward, the staple displaces the retainer spring, the staple forms on the flange and the retainer spring moves back to its initial position. On releasing the trigger and advancing the instrument the formed staple is separated from the flange, the second bias means returns the trigger and the forming blade to their initial positions, and the first bias means activates the staple advancing means to place the forwardmost staple adjacent the anvil surface.

An alternative surgical stapling instrument comprising a handle and a trigger pivotally attached and on compression internal to said handle has also been invented. The forward portion of the handle contains: a track; a leaf spring on the terminal end of said track; a plurality of staples loaded and staple advancing means carried on said track; a track cover mounted on said track; an anvil surface mounted and a first bias means movably mounted on the cover, the said anvil surface terminating in a perpendicular flange; and a staple adjacent said anvil surface separated from said flange by said leaf spring.

The forward portion of the handle also contains a guide block which is mounted on the track cover adjacent the anvil surface.

A forming blade and a second bias means are movably mounted on the guide block, the forming blade and the trigger having coordinating surfaces.

On compressing the trigger into the handle, the forming blade pushes the staple downward, the staple displaces the leaf spring, the leaf spring moves back to its initial position and the staple forms on the flange. On releasing the trigger and advancing the instrument, the formed staple is separated from the flange, the second bias means returns the trigger and the forming blade to their initial positions, and the first bias means activates the staple advancing means to place the forwardmost staple adjacent the anvil surface.

In one embodiment the stapling instrument described above comprises a track cover adjacent the forward portion of the trigger. In another embodiment the stapling instrument comprises the forming blade located between the forward portion of the track cover and the anvil surface.

In yet another embodiment the stapling instrument described above comprises an indicator to indicate the number of staples remaining in the instrument. The indicator has an initial end visible in the handle. A terminal end is movably mounted on the staple advancing means such that on releasing the trigger, the first bias means pulls the terminal end and thus moves the initial end of the indicator.

A method of using the stapling instrument is within the scope of this invention.

A method of closing a wound or of connecting skin or fascia comprises: joining the adjacent edges of the wound or skin or fascia; placing the stapling instrument described above adjacent to the wound or to the skin or fascia; compressing the trigger into the handle; and releasing the trigger and advancing the instrument, whereby a formed staple is placed between the edges.

DESCRIPTION OF THE PREFERRED EMBODIMENT

Figures 1, 2, 3:
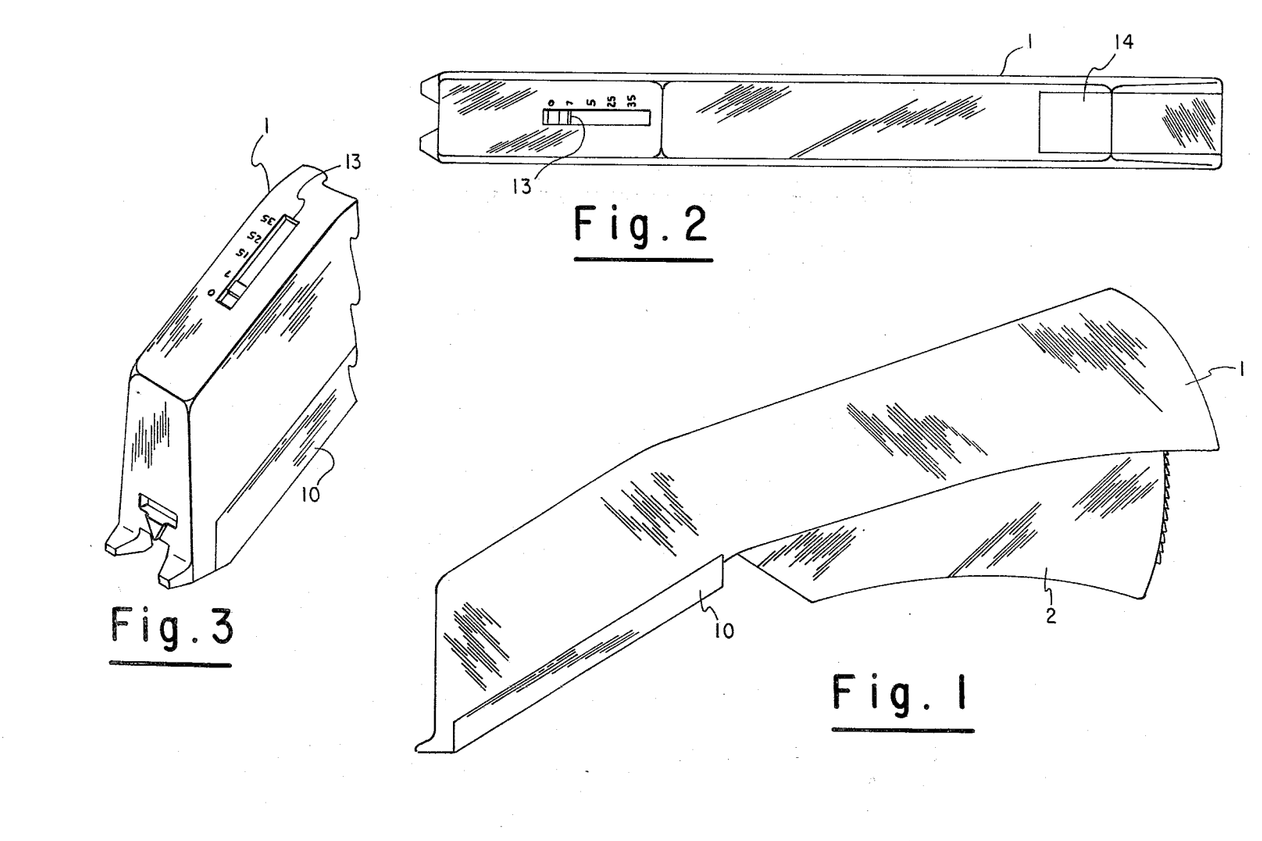
FIGS. 1 and 2 are side and top views respectively of the stapling instrument.
FIG. 3 is a broken perspective view of the front portion of the instrument shown in FIGS. 1 and 2.

Referring to FIGS. 1 to 3, the instrument comprises a handle 1 and a trigger 2. A staple track 10 (more fully described in FIGS. 6 and 9 to 10) is inserted and attached to the forward portion of the handle 1, for example by cementing or sonic welding. The initial end of an indicator 13 is visible through an opening in the forward top portion of the handle 1. A combined ratchet stop and cover 14 (more fully described in FIGS. 4 and 5) is attached to the rear portion of handle 1.

Referring to FIGS. 6 to 11 and 17, the track cover 3 is assembled as follows. The first bias means 7, which preferably is a negatory spring, is mounted into the openings 3a in track cover 3. Retainer spring 15 is inserted onto bending anvil retainer tabs 9a. The bending anvil 9 and the retainer spring 15 are then placed through the opening 3b. The terminal end 13a of indicator 13 is mounted onto the track cover 3 in front of the spring 7 and protrudes through the bottom 3c of the track cover 3.

The guide block 4 is mounted under tabs 3d. A locking wedge 8 is then pushed into slots 3e to hold the guide block 4 on the track cover 3. Other means for holding the guide block on the track cover can be used, for example bonding, riveting, peening, tacking or welding.

The second bias means 6, preferably a spring, is inserted into the guide block opening 4a. The forming blade 5 is mounted through the guides 4b in the guide block. The vertical surface of the forming blade 5 is between the forward portion 3i of the track cover 3 and anvil surface 9.

Figure 9:
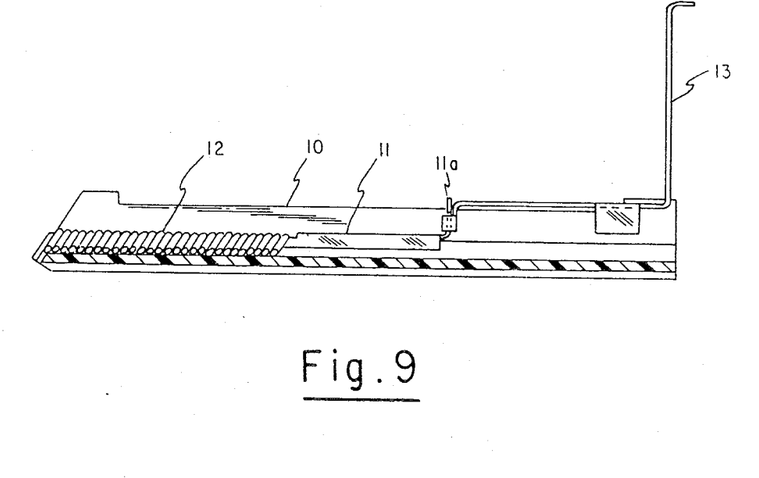
FIGS. 9 and 10 are sectional side, and top views respectively of the instrument track.
Figure 10:
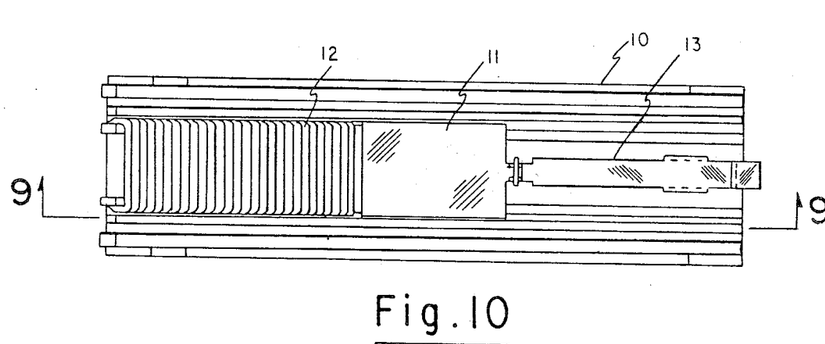
Figure 11:
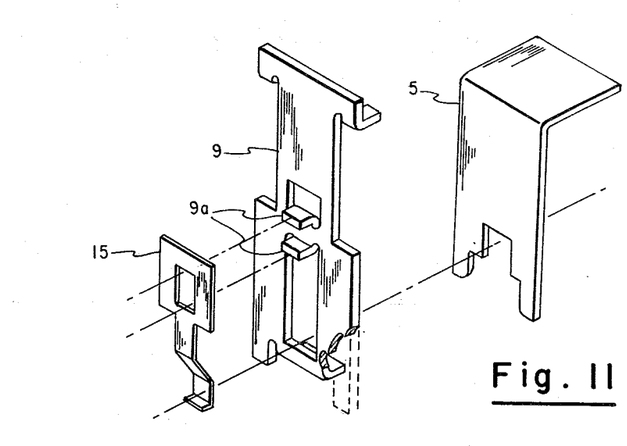
FIG. 11 is an expanded view showing the relationship of the forming blade, bending anvil and retainer spring.

Referring specifically to FIGS. 9 and 10, staples 12 are loaded onto the track 10. The staple advancing means, preferably a staple pusher 11 is carried on the track 10 behind the staples 12 by the first bias means 7 (shown e.g., in FIG. 8). The indicator 13 is carried with the staple pusher 11 by the first bias means 7. The staples 12 in FIGS. 9 and 10 are shown in their orientation when the instrument is in the position shown in FIG. 1.

The track cover 3 is then mounted onto the track 10 for example by sonic welding. The spring 7 is then attached to the advancing means tab 11a by pulling back on the indicator 13 and engaging the center of the extended spring 7 with the advancing means tab 11a. The trigger pivots 2aa placed against stops in the forward portion of the handle 1. The track cover 3 and track 10 are then inserted and attached to the forward portion of the handle 1, for example by cementing or sonic welding. The trigger pivots 2a are thus captured.

Referring to FIGS. 12 to 17, the stapling instrument is used by placing the anvil surface 9 adjacent a wound opening or between skin or fascia. The trigger 2 is then compressed into the handle 1 (shown in FIG. 1). The front end of trigger 2 engages the top flange of forming blade 5, forcing it down thru the guides 4b on guide block 4. The lower edges of the forming blade have a recessed area to engage staple 12. The staple is pushed downward and forced to bend at right angles on either side of the lower flange of anvil 9.

Figure 12:
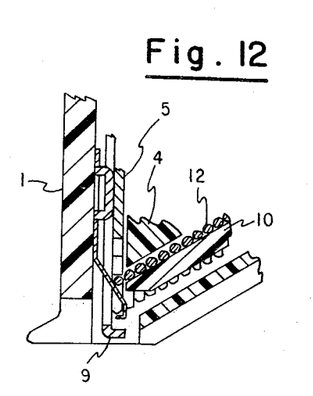
FIGS. 12 and 13 are broken and sectional side views of FIG. 1 showing the position and relationship of the staple and retainer spring in the initial position and on compressing the instrument trigger.

In the initial or rest position, the staple 12 is adjacent the vertical surface of the anvil 9, as shown in FIG. 12. The forming blade 5 lowers and pushes the staple downward and onto the anvil flange. The forming of the staple around the anvil lower flange is well known in prior art, e.g., as described in U.S. Pat. No. 4,014,492, issued Mar. 29, 1977, which is incorporated herein by reference. By releasing the trigger and advancing the instrument, the staple 12 is separated from the anvil flange.

Figure 13:
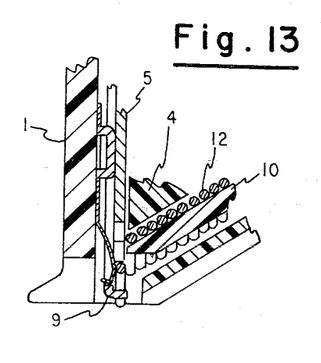
Figures 14, 15:
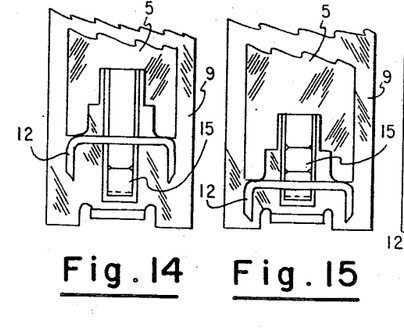
FIGS. 14 to 16 are broken rear views of the bending anvil showing the relationship of the staple, forming blade, retainer spring and anvil flange during compression of the instrument trigger.
Figure 16:
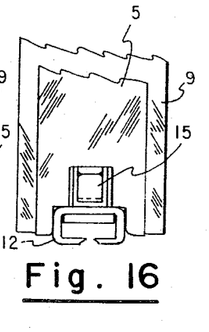

When releasing trigger 2, spring 6 returns forming blade 5 and trigger 2 to their relaxed positions. Spring 7 pulls against pusher 11 to advance the plurality of staples. Each time trigger 2 is compressed indicator 13 advances with pusher 11. An indication of the staple depletion appears in the opening in the top forward portion of handle 1.

Figures 4A, 4B:
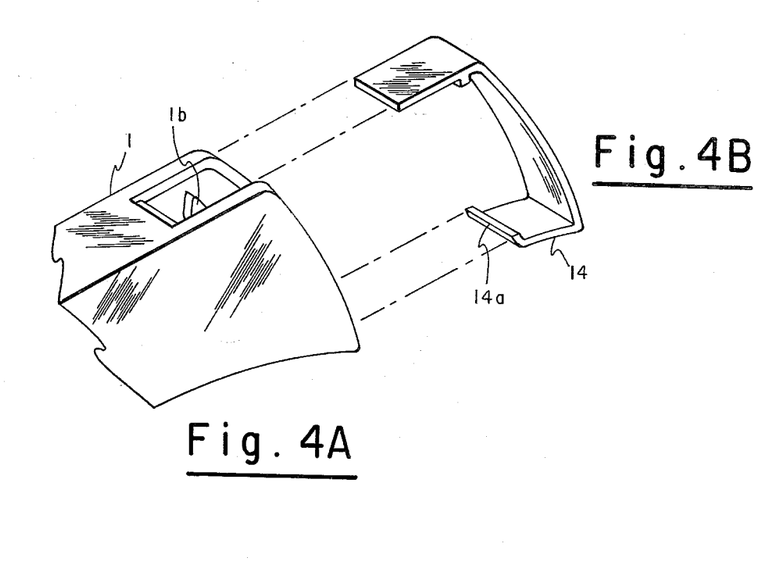
FIGS. 4A and 4B are perspective views showing the parts of the stapling instrument control means in the handle and in the handle cover, respectively.
Figure 5:
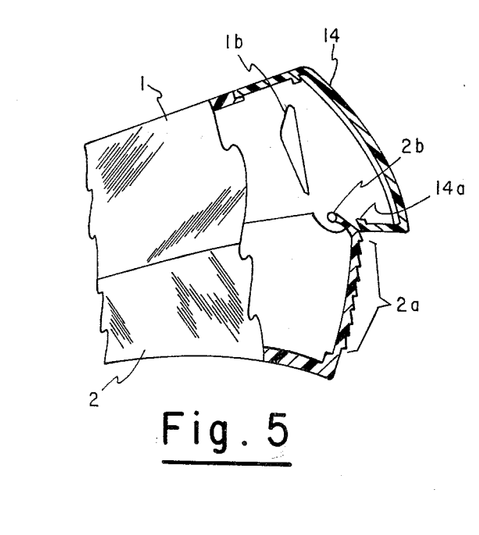
FIG. 5 is a broken sectional view of the stapling instrument control means.

Referring to FIGS. 4 and 5, to prevent partially compressing the trigger 2, partially forming a staple 12, and then allowing the trigger to return and pick up the next staple, a multi-toothed ratchet 2a is built into the rear of the trigger 2 and cam guides 1b into handle 1. When the trigger 2 is compressed, the ratchet 2a engages stop 14a and prevents the trigger from returning to its relaxed position. The trigger must be compressed past the last ratchet tooth 2a and must be completely closed so that the guide pins 2b (more fully shown in FIG. 6) move up and cross over the cam guides 1b.

The guide pins are spring loaded. Thus when the trigger is completely compressed, the guide pins cross over the top of the cam guides 1b. On releasing the trigger from a final compression, the ratchet is thus prevented from locking on the stop 14a.

Figures 18A, 18B, 19:
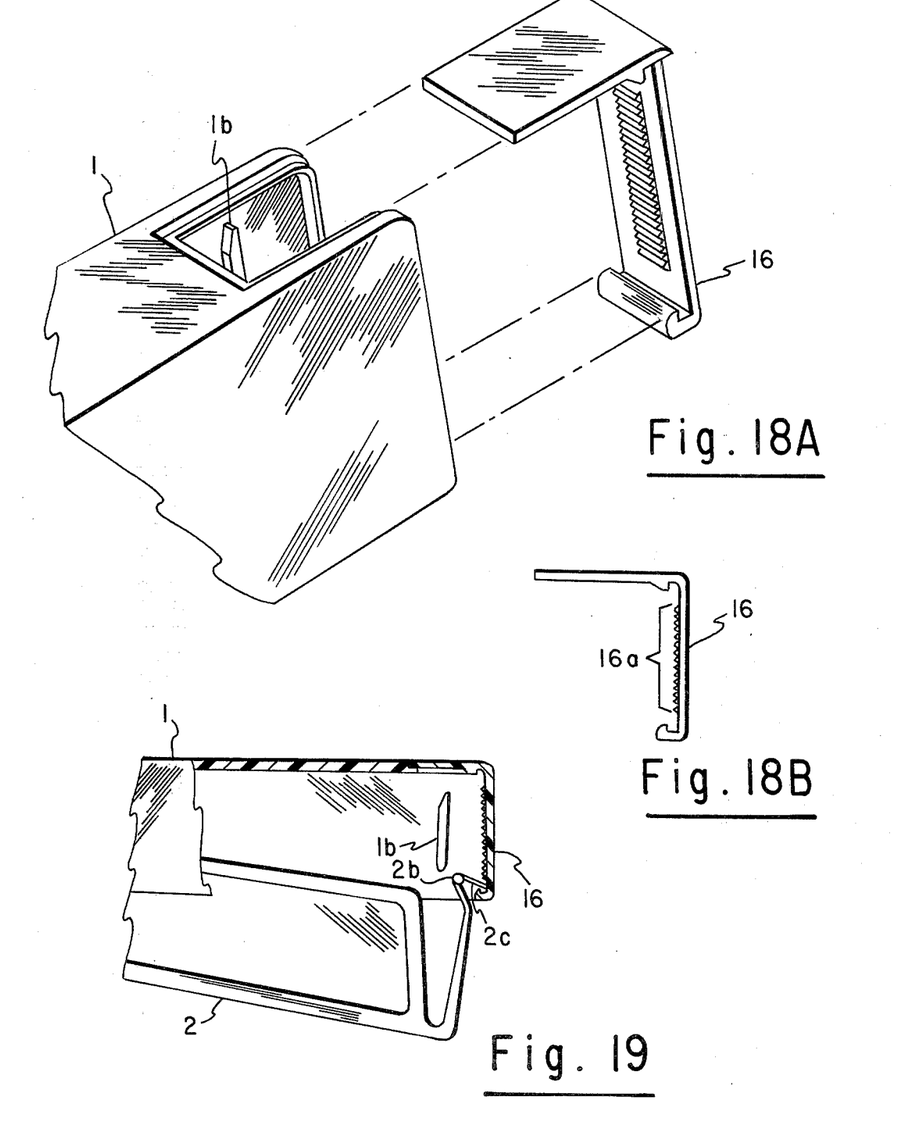
FIGS. 18A and 18B are perspective views showing an alternative embodiment of the stapling instrument control means.
FIG. 19 is a broken sectional view of the alternative stapling instrument control means of FIG. 18.

Referring to FIGS. 18 and 19 showing an alternative embodiment of the stapling instrument control means, to prevent partially compressing the trigger 2, partially forming a staple 12, and then allowing the trigger to return and pick up the next staple, a multi-toothed ratchet 16a is built into the cover 16. A stop 2c is built into the trigger 2. Cam guides 1b are built into handle 1. When the trigger 2 is compressed, the ratchet 16a engages stop 2c and prevents the trigger from returning to its relaxed position. The trigger must be compressed past the last ratchet tooth 16a and must be completely closed so that the guide pins 2b (more fully shown in FIG. 6) move up and cross over the cam guides 1b.

The guide pins 2b are spring loaded. Thus when the trigger is completely compressed, the guide pins cross over the top of the cam guides 1b. On releasing the trigger from a final compression, the ratchet is thus prevented from locking on the stop 2c.

Figures 20, 22, 23:
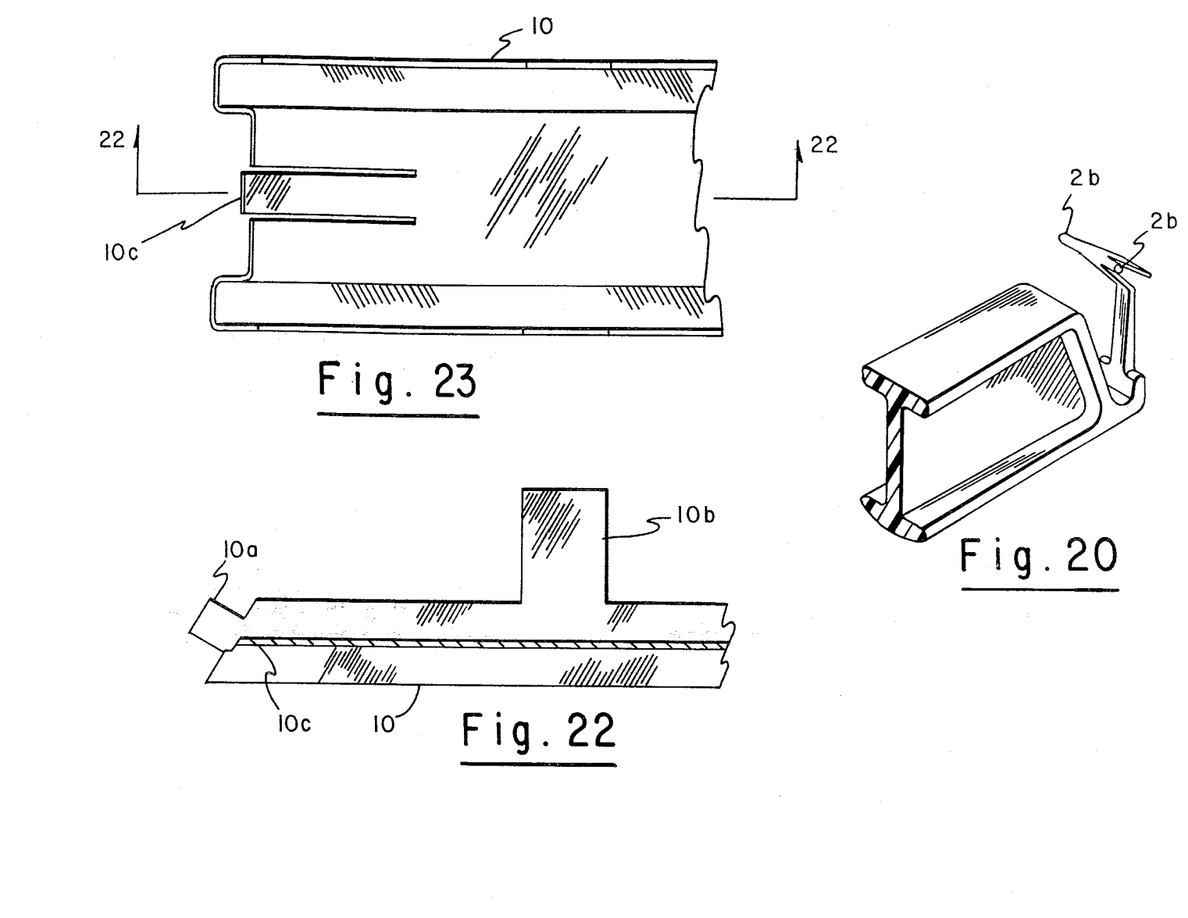
FIG. 20 is a broken perspective view of the alternative control means in the trigger.
FIGS. 22 and 23 are broken sectional side and top views, respectively of the instrument track shown in FIG. 21.
Figure 21:
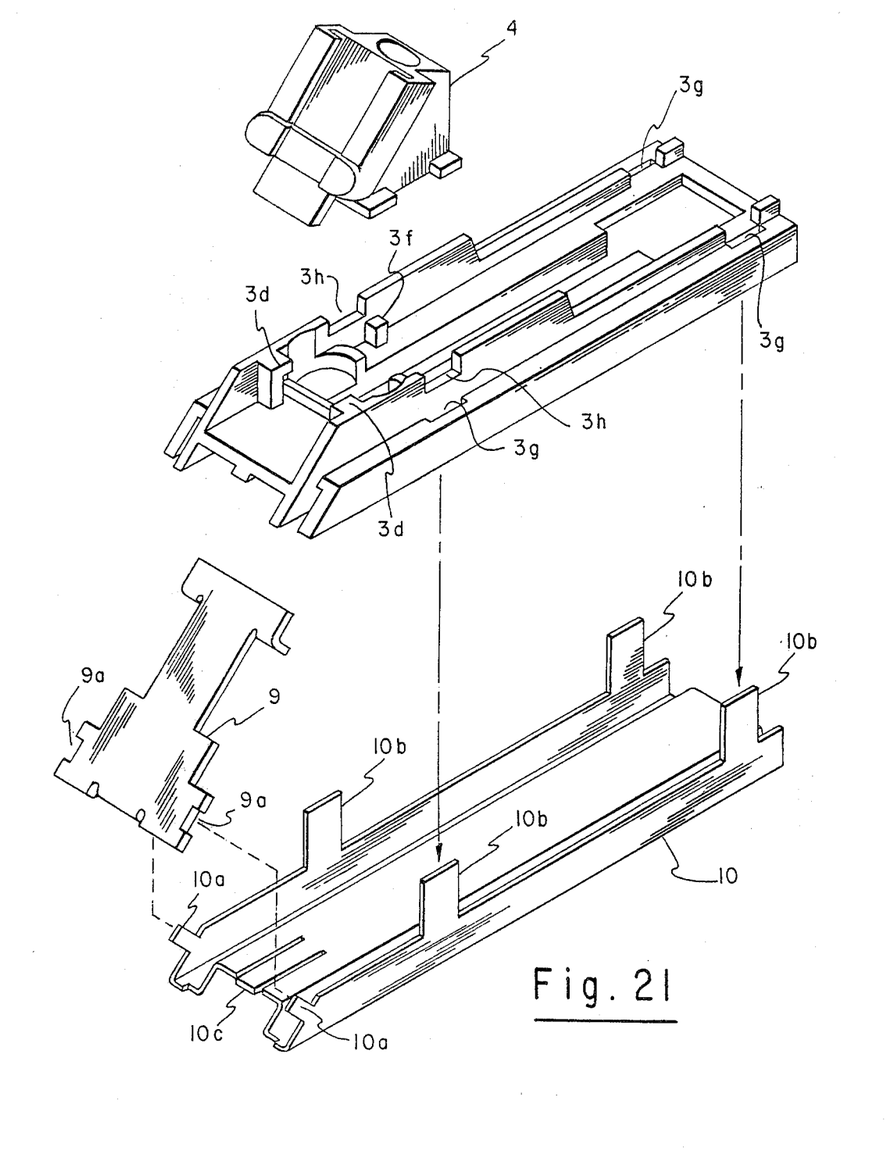
FIG. 21 is an expanded view of an alternative embodiment of the track and track cover.
Figure 24:
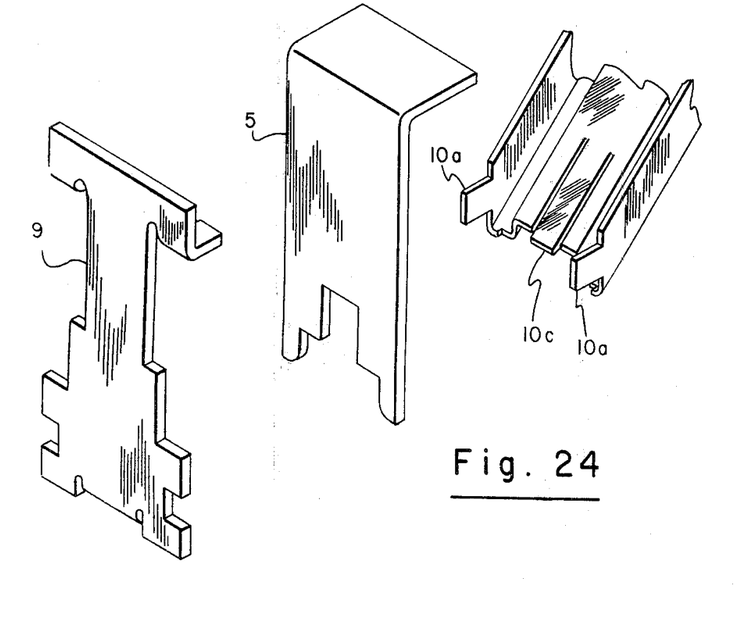
FIG. 24 is an expanded view showing the relationship of the forming blade, bending anvil and leaf spring shown in FIG. 21.

Referring to FIGS. 20 and 21 which show respectively, the alternative control means in the trigger and an alternative embodiment of the track and track cover, the track cover 3 is assembled as follows. The forward portion 3i of the track cover can be identical to that shown in FIGS. 6 to 8. The bias means 7 (not shown) and the bending anvil 9 are mounted identically to the description in FIGS. 6 to 8 and 17. The front tabs 10a on the track 10 pass through the slots 9a and then fold onto the bending anvil 9. As shown more fully in FIG. 24, the front tabs 10a and the slots 9a are sufficiently wide to allow the forming blade 5 to move. The terminal end 13a of indicator 13 (not shown) is mounted identically to the description in FIGS. 6 to 10.

The guide block 4 is mounted under tabs 3d as shown in FIGS. 6 to 8 and 17. Blocks 3f are adjacent slots 3h on the track cover 3. Blocks 3f diagonally support the guide block 4 on the track cover 3. Forward vertical tabs 10b on the track 10 pass through the forward openings 3g in the track cover 3 and then fold onto the portion of the guide block 4 in slots 3h to hold the guide block on the track cover. Rear vertical tabs 10b pass through the rear openings 3g and then fold onto the track cover 3.

Figure 6:
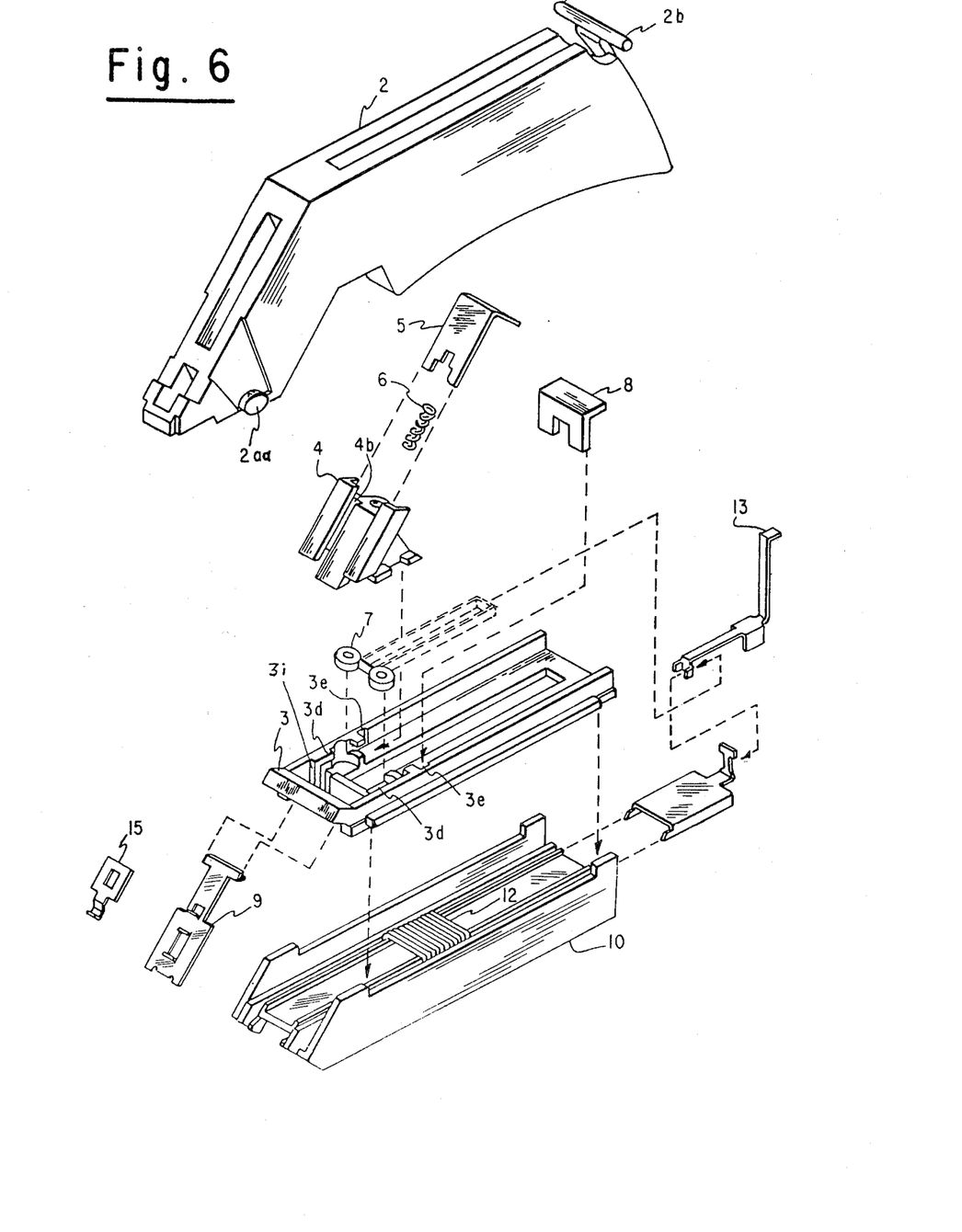
FIG. 6 is a perspective view of the instrument trigger, and an expanded view of the track and track cover.
Figure 7:
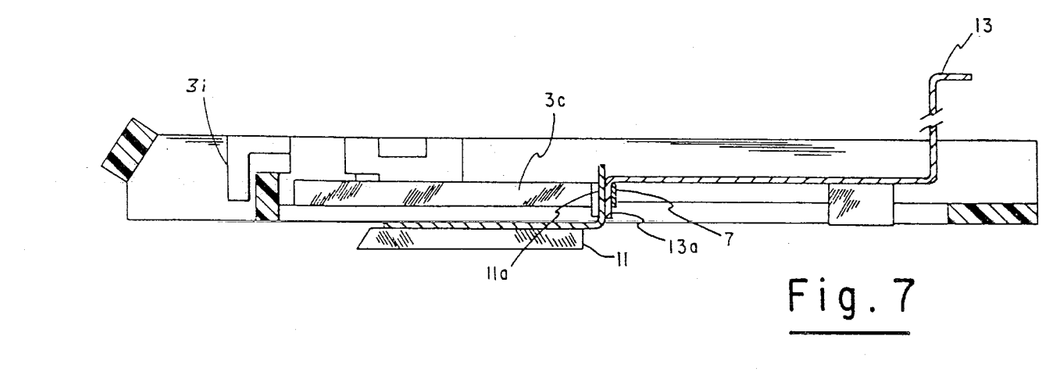
FIGS. 7 and 8 are sectional side, and top views respectively of the instrument track cover.
Figure 8:
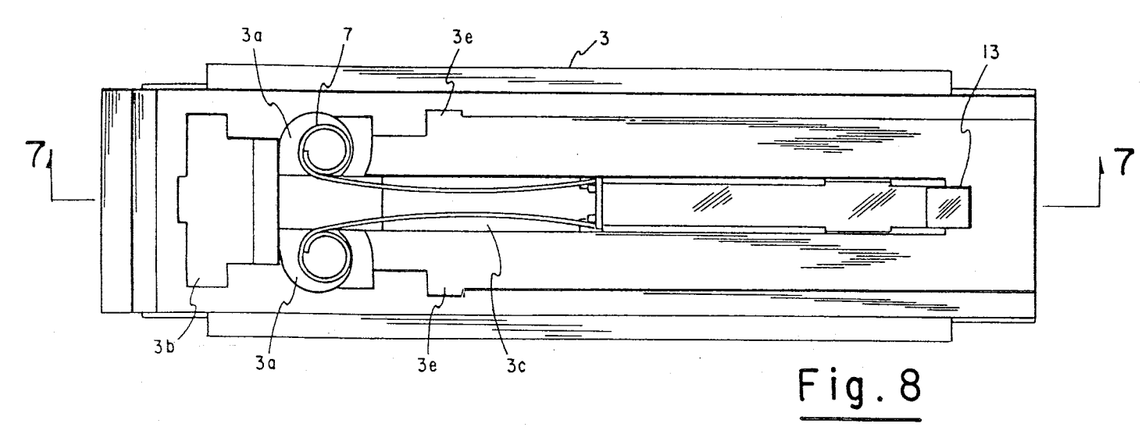
Figure 17:
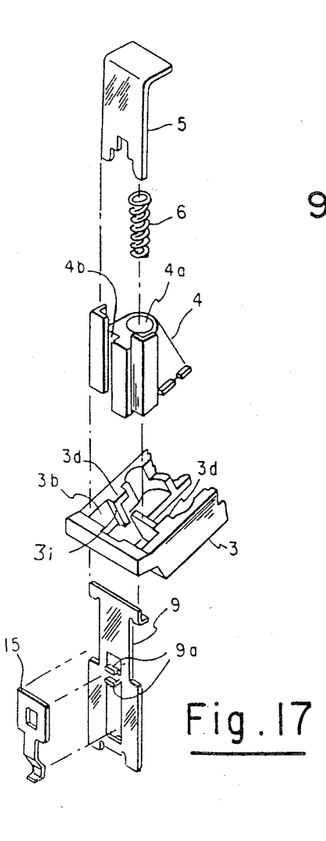
FIG. 17 is an expanded view showing the relationship of the forming blade, first bias means, guide block, track cover, bending anvil and retainer spring.

The second bias means 6 and the forming blade 5 are mounted identically to the description in FIGS. 6 and 17.

FIGS. 22 and 23 show an alternative embodiment of the track 10. In the alternative embodiment, the track 10 contains a leaf spring 10c on the terminal end of the track. The leaf spring separates the staple adjacent to the anvil surface from the anvil flange. The staples 12, staple advancing means 11, and indicator 13 are carried on the track 10 and are identical to the description in FIGS. 9 and 10. Referring to FIGS. 22 to 27, the stapling instrument with the alternative embodiments is used by placing the anvil surface 9 adjacent a wound opening or between skin or fascia. The trigger 2 (shown in FIG. 1) is then compressed into the handle 1. The front end of trigger 2 engages the top flange of forming blade 5, forcing it down thru the guides 4b (shown in FIG. 17) on guide block 4. The lower edges of the forming blade have a recessed area to engage staple 12. The staple is pushed downward and displaces the leaf spring 10c. The leaf spring 10c then moves back to its initial position to hold the next staple at the terminal end of track 10 and adjacent the anvil surface. The forming blade 5 continues to engage staple 12 which is then forced to bend at right angles on either side of the lower flange of anvil 9.

Figure 25:
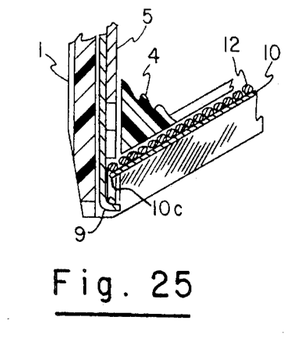
FIGS. 25 to 27 are broken and sectional side views showing respectively the position and relationship of the staple and leaf spring in the initial position, on partial compressing and on complete compressing of the instrument trigger.
Figure 26:
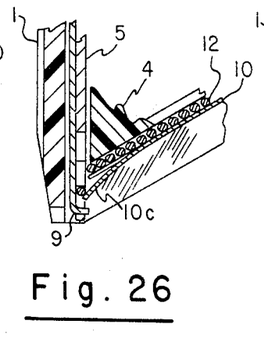
Figure 27:
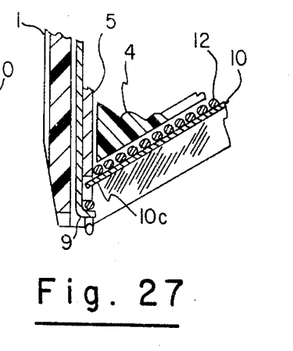

In the initial or rest position, the staple 12 is adjacent the vertical surface of the anvil 9, as shown in FIG. 25. The forming blade 5 lowers and pushes the staple downward and onto the anvil flange. By releasing the trigger and advancing the instrument, the staple 12 is separated from the anvil flange.

We claim:
1. A surgical stapling instrument comprising a handle; a trigger pivotally attached and compressible into said handle, the forward portion of said handle containing:
   a track;
   a leaf spring contained on the terminal end of said track, a portion of said leaf spring extending beyond said track;
   a plurality of staples loaded and staple advancing means carried on said track;
   a track cover mounted on said track;
   an anvil surface mounted, and a first bias means movably mounted on the cover, the said anvil surface terminating in a perpendicular flange;
   the proximal staple, from said plurality of staples, adjacent said anvil surface, and separated from said flange by the underside of said staple being biased by said leaf spring;
   a guide block mounted on said cover adjacent said anvil surface; and
   a forming blade and a second bias means movably mounted on said guide block, the front end of said trigger engaging said forming blade such that on compressing said trigger into said handle, said forming blade pushes said staple downward, said staple displaces said leaf spring, said leaf spring moves back to its initial position and said staple forms on said flange; and on releasing said trigger and advancing said instrument said formed staple is separated from said flange, said second bias means returns said trigger and said forming blade to their initial positions, and said first bias means activates said staple advancing means to place the forwardmost staple adjacent said anvil surface.

2. A stapling instrument of claim 1 wherein said cover is adjacent the forward portion of said trigger.

3. A stapling instrument of claim 2 wherein said forming blade is between the forward portion of said cover and said anvil surface.

4. A stapling instrument of claim 1 or 2 or 3 containing an indicator having an initial end visible in a portion of said handle opposite said trigger and a terminal end movably mounted on said advancing means such that on releasing said trigger, said first bias means pulls the terminal end and thus moves the initial end of said indicator to indicate the number of staples remaining.

* * * * *